United States Patent
Narayanan

(10) Patent No.: US 6,919,100 B2
(45) Date of Patent: Jul. 19, 2005

(54) METHOD FOR COATING MEDICAL DEVICES

(75) Inventor: Pallassana V. Narayanan, Belle Mead, NJ (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 10/349,457

(22) Filed: Jan. 22, 2003

(65) Prior Publication Data

US 2004/0142094 A1 Jul. 22, 2004

(51) Int. Cl.[7] .............................. B05D 1/18; A61L 27/00
(52) U.S. Cl. ....................... 427/2.24; 427/2.1; 427/2.25; 427/2.26; 427/2.28; 427/2.3; 427/2.31; 427/430.1; 472/435; 472/402; 472/409; 472/407.1
(58) Field of Search ................................ 427/2.1, 2.24, 427/2.25, 2.26, 2.28, 2.3, 2.31, 430.1, 435, 402, 409, 407.1

(56) References Cited

U.S. PATENT DOCUMENTS

| | | | |
|---|---|---|---|
| 3,929,992 A | | 12/1975 | Sehgai et al. |
| 4,675,347 A | | 6/1987 | Mochizuki |
| 5,756,144 A | * | 5/1998 | Wolff et al. ................... 427/2.3 |
| 6,153,252 A | * | 11/2000 | Hossainy et al. ............ 427/2.3 |
| 6,196,432 B1 | | 3/2001 | Faliano |
| 6,283,238 B1 | | 9/2001 | Royer |
| 6,352,187 B2 | | 3/2002 | Strode |
| 2002/0051730 A1 | * | 5/2002 | Bodnar et al. ................ 422/33 |

FOREIGN PATENT DOCUMENTS

| | | |
|---|---|---|
| EP | 0214721 A | 3/1987 |
| WO | WO 02/10278 A | 2/2002 |

* cited by examiner

Primary Examiner—Jennifer Kolb Michener

(57) ABSTRACT

Medical devices, and in particular implantable medical devices, may be coated to minimize or substantially eliminate a biological organism's reaction to the introduction of the medical device to the organism or to treat a particular condition. A dip coating process is utilized to minimize waste. An aqueous latex polymeric emulsion is utilized to coat any medical device to a desired thickness by allowing for successive dipping and drying cycles. In addition, aqueous latex polymeric emulsions pose less of a chance of the bridging phenomenon associated with organic solvent based polymers.

10 Claims, 2 Drawing Sheets

METHOD FOR COATING MEDICAL DEVICES

BACKGROUND OF THE INVENTION

1. Field of the Invention

The present invention relates to a process for coating medical devices, and more particularly, to a process for dip coating medical devices having complex configurations or geometries utilizing aqueous latex polymeric emulsions.

2. Discussion of the Related Art

Stents, which are generally open tubular structures, have become increasingly important in medical procedures to restore the function of body lumens. Stents are now commonly used in translumenial procedures such as angioplasty to restore an adequate blood flow to the heart. However, stents may stimulate foreign body reactions that result in thrombosis or restenosis. To avoid these complications, a variety of polymeric stent coatings and compositions have been proposed in the literature, both to reduce the incidence of these or other complications or by delivering therapeutic compounds such as thrombolytics to the lumen to prevent thrombosis or restenosis. For example, stents coated with polymers containing thrombolytics such as heparin have been proposed in the literature.

Stents are typically coated by a simple dip or spray coating of the stent with polymer or polymer and a pharmaceutical/therapeutic agent or drug. These methods were acceptable for early stent designs that were of open construction fabricated from wires or from ribbons. Dip coating with relatively low coating weights (about four percent polymer) could successfully coat such stents without any problems such as excess coating bridging, i.e. forming a film across the open space between structural members of the device. This bridging is of particular concern when coating more modern stents that are of less open construction. Bridging of the open space (slots) is undesirable because it can interfere with the mechanical performance of the stent, such as expansion during deployment in a vessel lumen. Bridges may rupture upon expansion and provide sites that activate platelet deposition by creating flow disturbances in the adjacent hemodynamic environment, or pieces of the bridging film may break off and cause further complications. Bridging of the open slots may also prevent endothelial cell migration, thereby complicating the endothelial cell encapsulation of the stent. The bridging problem is of particular concern in medical devices having complex configurations or designs, such as stents, which comprise a multiplicity of curved surfaces.

Similarly, spray coating can be problematic in that there is a significant amount of spray lost during the spray process and many of the pharmaceutical agents that one would like to incorporate in the device are quire costly. In addition, in some cases it would be desirable to provide coated stents with high levels of coating and drug. High concentration coatings (approximately fifteen percent polymer with additional drug) are the preferred means to achieve high drug loading. Multiple dip coating has been described in the literature as a means to build thicker coatings on the stent. However, composition and phase dispersion of the pharmaceutical agents affect sustained release profile of the pharmaceutical agent. In addition, the application of multiple dip coats from low concentration solutions often has the effect of reaching a limiting loading level as an equilibrium state is reached between the solution concentration and the amount of coating, with or without pharmaceutical agent, deposited on the stent. Thus there is a continuing need for new and improved stent coating techniques.

Another potential problem associated with coating stents and other implantable medical devices having complex designs or configurations is the use of organic based solvents. Presently, polymeric coatings are applied from solutions of one or more polymers in one or more organic solvents. These solvents do not permit repeated dipping to build up the desired amount of coating as the solvent will re-dissolve the coating applied during the previous dipping. Accordingly, spin or spray coating techniques are utilized. However, as described above, this type of coating process may result in a significant amount of material lost.

Spray coating utilizing organic solvents generally involves dissolving a polymer or polymers and a therapeutic agent or agents in an organic solvent or solvents. The polymer(s) and therapeutic agent(s) may be dissolved at the same time or at different times, for example, it may be beneficial to add the therapeutic agent(s) just prior to coating because of the short shelf-life of the agent(s). Certain therapeutic agents may be dissolved in organic solvents while others may not. For example, rapamycin may be mixed with poly-(vinylidenefluoride)-co-hexafluoropropylene and dissolved in a mixture of methyl ethyl ketone (MEK) and dimethylacetamide (DMAC) for use as a coating on a stent to prevent or substantially minimize restenosis. Water based therapeutic agents may not be dissolvable in organic solvents, although it may be possible to disperse very fine powder form therapeutic agents in an organic solvent polymer emulsion. Therefore, whole classes of therapeutic agents may not be available for use in local delivery applications on implantable medical devices.

In addition, organic solvents may be difficult to work with due to their potentially flammable or combustible nature.

Accordingly, there exists a need for a coating process that allows for the safe, efficient, cost effective coating of medical devices for a wide range of polymers and therapeutic drugs, agents and/or compounds.

SUMMARY OF THE INVENTION

The present invention overcomes the disadvantages associated with coating medical devices, as briefly described above, by utilizing an aqueous latex emulsion of polymers and therapeutic drugs, agents and/or compounds in a dip coating process.

In accordance with one aspect, the present invention is directed to a method for coating medical devices. The method comprises the steps of preparing an aqueous latex polymeric emulsion, dipping a medical device in the aqueous latex polymeric emulsion, drying the aqueous latex polymeric emulsion on the medical device, and repeating the dipping and drying steps until the aqueous latex polymeric emulsion coating reaches a predetermined thickness.

In accordance with another aspect, the present invention is directed to a method for coating medical devices. The method comprises the steps of preparing an aqueous latex polymeric emulsion, adding at least one drug, agent and/or compound, in therapeutic dosages, to the aqueous latex polymeric emulsion for the treatment of a predetermined condition, dipping the medical device in the aqueous latex polymeric emulsion, including the at least one drug, agent and/or compound, drying the aqueous latex polymeric emulsion, including the at least one drug, agent and/or compound, on the medical device to form a coating thereon, and repeating the dipping and drying steps until the aqueous latex polymeric emulsion, including the at least one drug, agent and/or compound coating reaches a predetermined thickness.

The method for dip coating medical devices in an aqueous latex polymeric emulsion, which may or may not include therapeutic drugs, agents and/or compounds, in accordance with the present invention provides a safe, efficient and effective process for coating medical devices having simple or complex configurations or designs. The dip coating process includes preparing an aqueous latex polymeric emulsion from any number of biocompatible monomers, adding drugs, agents and/or compounds in therapeutic dosages to the polymeric emulsion if desired to treat a specific condition, dipping the medical device in the emulsion, including any drug, agent and/or compound added thereto, allowing the polymeric emulsion to dry on the medical device thereby forming a coating thereon, and repeating the dipping and drying steps until the desired coating thickness is achieved. The drug, agent and/or compound may be added to the emulsion as solid(s) or solution(s). The medical device may be dried by allowing the water to evaporate or by utilizing a drying device such as a fan.

The method in accordance with the present invention minimizes waste. Spray coating of medical devices results in waste because of the overspray phenomenon. This waste may result in significant material and monetary losses, especially if drugs, agents and/or compounds are utilized. Desired coating thicknesses may also be achieved by utilizing a dip coating process with an aqueous latex polymeric emulsion. In organic based solvent polymeric emulsions, repeated dipping dissolves the previously laid down layers. The aqueous latex polymeric emulsion of the present invention enables multiple dippings without dissolving the material laid down during the prior dipping steps and thus build up a coating of desired weight or thickness. In addition, medical devices having complex configurations or geometries, may be coated more effectively since aqueous latex polymeric emulsions are substantially less likely to bridge gaps between the structural members of the medical devices.

The method in accordance with the present invention is safe to implement. Water based emulsions are safer to utilize because there is little chance of fire or explosion. In addition, it is safer from the disposal perspective. Organic based solvent polymeric emulsion disposal must be done in accordance with strict environmental guidelines, whereas water based polymeric emulsions are much more easily disposed of.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
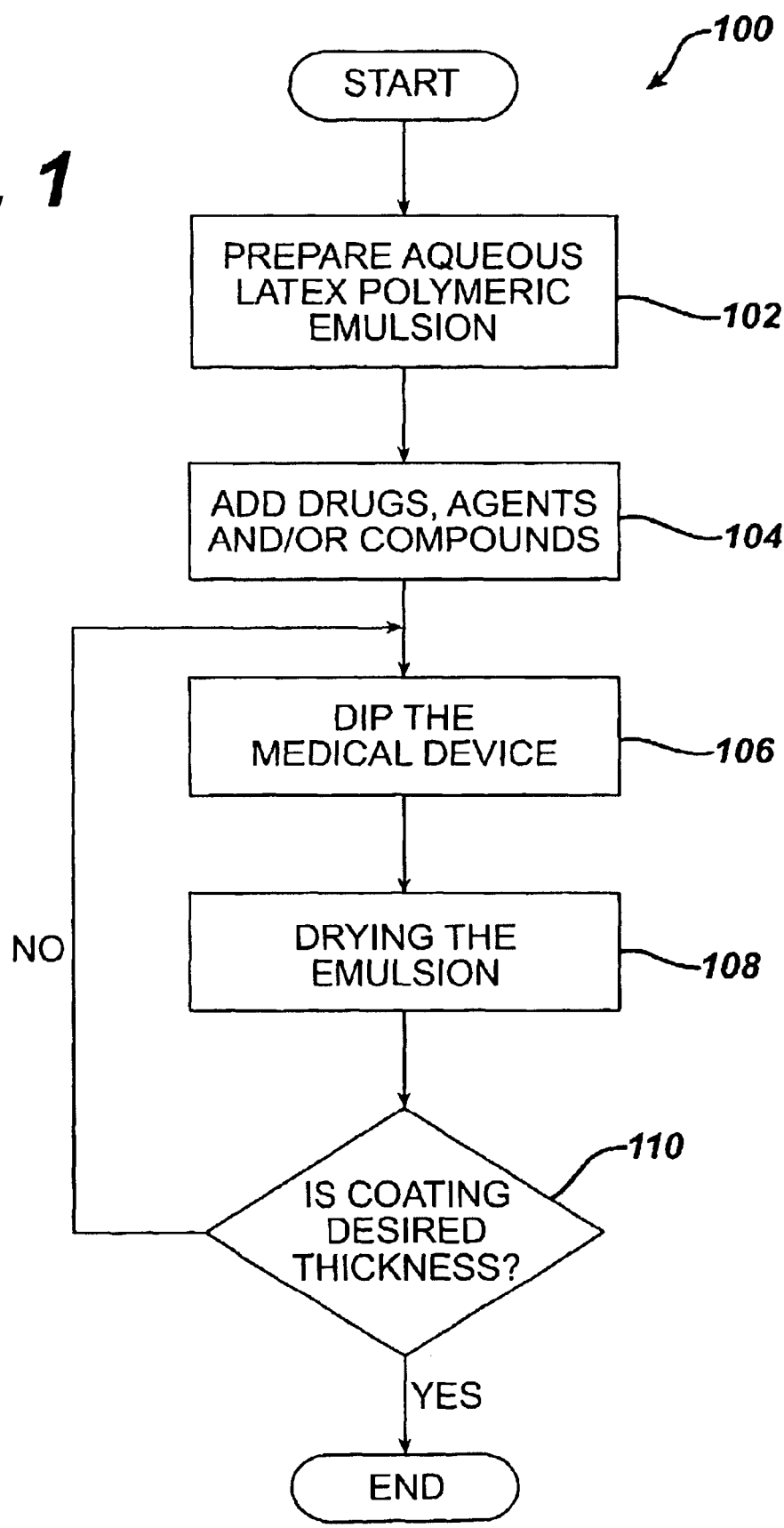
FIG. 1 is a flow chart of the method for coating medical devices in accordance with the present invention.

The local delivery of drug/drug combinations may be utilized to treat a wide variety of conditions utilizing any number of medical devices, or to enhance the function and/or life of the medical device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes— dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The present invention is directed to a method of dip coating medical devices in an aqueous latex (includes stable aqueous dispersions of natural rubber, synthetic rubber and vinyl polymers prepared by emulsion polymerization) polymeric emulsion, which may or may not include therapeutic drugs, agents and/or compounds. In utilizing a dip coating process, waste is minimized as compared to a spray coating process. Also, by utilizing an aqueous latex polymeric emulsion, the dip coating process may be repeated until the desired coating thickness is achieved. In other words, greater control over the weight and thickness of the coating may be achieved. In addition, medical devices having complex configurations or geometries, for example, stents, may be coated more effectively since aqueous latex polymeric emulsions are substantially less likely to bridge gaps between the structural members of the medical devices as described above.

Referring to FIG. 1, there is illustrated a flow chart 100 of the method for coating medical devices. The dip coating process includes preparing an aqueous latex polymeric emulsion 102, adding drugs, agents and/or compounds in therapeutic dosages to the polymeric emulsion, if desired 104, dipping the medical device in the polymeric emulsion 106, allowing the polymeric emulsion to dry on the medical device 108, determining if the coating is of the desired thickness 110, and repeating steps 106 to 110 until the desired coating thickness is achieved. Typically, the coating thickness is in the range from about four microns to about one hundred microns, and preferably in the range from about four microns to about fifteen microns.

Although any number of biocompatible polymers may be utilized in accordance with the present invention, the exemplary aqueous latex polymeric emulsion is formed from two monomers, vinylidenefluoride and hexafluoropropylene. Each of these monomers are gases at atmospheric pressure; accordingly, the polymerization reactor is pressurized to a pressure in the range from about five hundred fifty psi to about one thousand eight hundred psi during the polymerization process, wherein the monomers are in the liquid state or phase. The monomers, in the liquid state, may be added to the water at the same time or at different times. The monomers are added to the water in a predetermined ratio by weight. The monomer to water ratio may be in the range from about 5:95 to about 35:65 and preferably about 25:75.

Polymerization is essentially the formation of compounds, usually of high molecular weight, containing repeating structural units from reactive intermediates or monomers. An initiator may be utilized to initiate the polymerization process. Since this is a water based polymer, any number of water soluble initiators may be utilized, including hydrogen peroxide or partially water soluble peroxides and azo compounds. In the exemplary embodiment, ammonium persulfate is added to the water and monomer mixture as an initiator. Water based initiators work by dissociating in water at elevated temperatures, controlled by the polymerization reactor, to form free radicals. The free radicals then initiate polymerization by reacting with a monomer molecule, creating a new free radical, which then continues the polymerization process until the monomer or monomers is/are is consumed.

Surfactants maintain molecules in suspension and prevents the constituents of an emulsion from aggregating. Essentially, surfactants act as emulsifying agents. It is possible to carry out the polymerization process without the use of surfactants. If no surfactant is utilized, initiator residue on the polymer chain end acts as a stabilizing agent to prevent polymer flocculation, i.e. aggregation. If a surfactant is utilized, any number of compounds may be utilized. In the exemplary embodiment, a blend of fluorinated surfactants, Fluorad FC-26 and Zonyl TBS is utilized. Fluorinated surfactants are utilized in the exemplary embodiment because of their compatibility with the fluorinated monomers. The surfactants work by forming micelles or surfactant-rich regions, within the aqueous medium, which act as loci for polymer initiation. As the polymer particles grow, the surfactant migrates to the outside of the polymer particles, with the hydrophobic (lacking affinity for water) end attached to the polymer and the hydrophilic (strong affinity for water) end extending into the aqueous medium or water. This action tends to stabilize the polymer particles thus preventing them from colliding and flocculating.

The combination of water, monomers, initiator and surfactants is constantly stirred or agitated throughout the entire polymerization process. Any suitable means may be utilized to agitate or stir the mixture within the polymerization reactor. The polymerization process may have a duration in the range from about two hours to about twenty hours. The polymerization process or reaction time is generally about seven hours depending on the desired level of conversion, initiator concentration and temperature. The polymerization reaction may be conducted at a temperature in the range from about seventy-five degrees C. to about one hundred ten degrees C. The length of the reaction time determines the ratio of monomers in the final polymer.

To increase the purity of the polymer, a nitrogen blanket is utilized in the polymerization reactor. Nitrogen is pumped into the reaction chamber in order to eliminate as much oxygen as possible so that as little oxygen as possible becomes incorporated into the polymer. Recalling that the polymerization reactor is pressurized to a pressure in the range from about five hundred fifty psi to about eighteen hundred psi, the nitrogen blanket may be utilized for this prupose.

Once the desired reaction time is achieved, the contents of the polymerization reactor are allowed to cool to ambient temperature and the closed system of the reactor is vented to atmospheric pressure. The venting of the polymerization reactor eliminates the nitrogen from the reactor and in the process removes any monomer residue. Monomer residue exists because one hundred percent conversion to polymer is difficult to achieve. Once the venting is complete, the polymerization reactor contains an aqueous latex polymer emulsion which may be utilized to coat medical devices.

A medical device may be dip coated in just the poly (vinylidenefluoride)/hexafluoropropylene aqueous latex polymeric emulsion or a mixture or dispersion of one or more therapeutic drugs, agents and/or compounds and the polymeric emulsion. Any number of drugs, agents and/or compounds, in therapeutic dosages, may be mixed with or dispersed in the polymeric emulsion. The drugs, agents and/or compounds may be in solid or liquid form. The drugs, agents and/or compounds may be soluable in water, for example, heparin, or not soluable in water, for example, rapamycin, which is discussed in detail subsequently. If the drugs, agents and/or compounds are not soluable in the aqueous latex polymeric emulsion, they may be dispersed throughout the polymeric emulsion by utilizing any number of well-known dispersion techniques.

The medical device, as described above, is dipped in the aqueous latex polymeric emulsion, with or without the drugs, agents and/or compounds. The medical device is then removed from the polymeric emulsion wherein the water evaporates and the remaining particulates forming the emulsion form a coating on the surfaces of the medical device and not in the gaps between sections of the device. As set forth above, the medical device may be assisted in drying through the use of fans, heaters, blowers or the like. Once the medical device is "dry" the thickness of the coating may be determined utilizing any number of measuring techniques. If a thicker coating is desired, the medical device may be repeatedly dipped and dried until the desired thickness is achieved. Upon successive dippings the water part of the emulsion will not re-dissolve the polymer that dried on the surfaces of the medical device. In other words, repeat dipping will not cause the particulate matter to re-disperse in the water. When organic solvents are utilized, as described above, repeat dipping cannot be successfully utilized.

The dip coating process of the present invention may be particularly useful in coating stents. Coronary stenting may be utilized to effectively prevent vessel constriction after balloon angioplasty. However, inasmuch as stents prevent at least a portion of the restenosis process, a combination of drugs, agents and/or compounds which prevent smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systematic use of drugs, agents and/or compounds in combination with the local delivery of the same or different drugs, agents and/or compounds may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, one stent is described in exemplary embodiments of the present invention. The skilled artisan will recognize that any number of stents, constructed from any number of materials, may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

Figure 2:
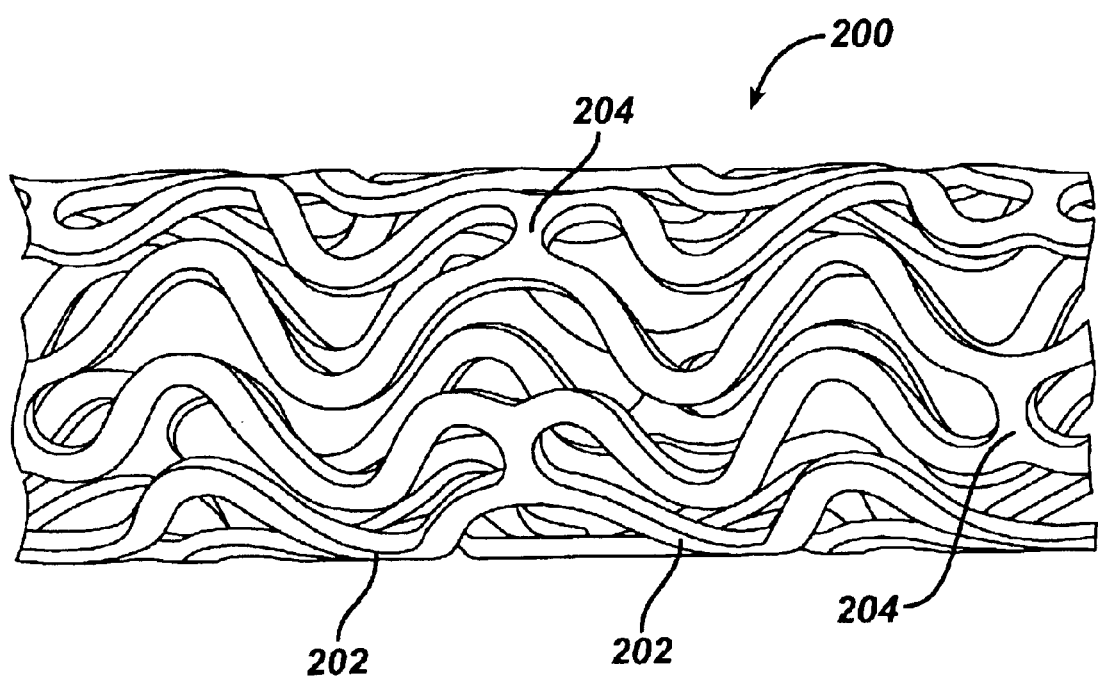
FIG. 2 is a view along the length of a stent (ends not shown) prior to expansion, showing the exterior surface of the stent and the characteristic banding pattern.

FIG. 2 illustrates an exemplary stent 200 which may be utilized in accordance with an exemplary embodiment of the present invention. The expandable cylindrical stent 200 comprises a fenestrated structure for placement in a blood vessel, duct or lumen to hold the vessel, duct or lumen open, more particularly for protecting a segment of artery from restenosis after angioplasty. The stent 200 may be expanded circumferentially and maintained in an expanded configuration, that is circumferentially or radially rigid. The stent 200 is axially flexible and when flexed at a band, the stent 200 avoids any externally protruding component parts.

The stent 200 generally comprises first and second ends with an intermediate section therebetween. The stent 200 has a longitudinal axis and comprises a plurality of longitudinally disposed bands 202, wherein each band 202 defines a generally continuous wave along a line segment parallel to the longitudinal axis. A plurality of circumferentially arranged links 204 maintain the bands 202 in a substantially tubular structure. Essentially, each longitudinally disposed band 202 is connected at a plurality of periodic locations, by a short circumferentially arranged link 204 to an adjacent band 202. The wave associated with each of the bands 202 has approximately the same fundamental spatial frequency in the intermediate section, and the bands 202 are so disposed that the wave associated with them are generally aligned so as to be generally in phase with one another. As illustrated in the figure, each longitudinally arranged band 202 undulates through approximately two cycles before there is a link to an adjacent band 202.

The stent 200 may be fabricated utilizing any number of methods. For example, the stent 200 may be fabricated from a hollow or formed stainless steel tube that may be machined using lasers, electric discharge milling, chemical etching or other means. The stent 200 is inserted into the body and placed at the desired site in an unexpanded form. In one exemplary embodiment, expansion may be effected in a blood vessel by a balloon catheter, where the final diameter of the stent 200 is a function of the diameter of the balloon catheter used.

It should be appreciated that a stent 200 in accordance with the present invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 200 has been formed it may be compressed so as to occupy a space sufficiently small as to permit its insertion in a blood vessel or other tissue by insertion means, wherein the insertion means include a suitable catheter, or flexible rod. On emerging from the catheter, the stent 200 may be configured to expand into the desired configuration where the expansion is automatic or triggered by a change in pressure, temperature or electrical stimulation.

The stent 200 may be coated with the aqueous latex polymeric emulsion described above, and any number of drugs, agents and/or compounds in therapeutic dosage amounts. Rapamycin has been shown to significantly reduce restenosis.

Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

As used herein, rapamycin includes rapamycin and all analogs, derivatives and congeners that bind to FKBP12, and other immunophilins and possesses the same pharmacologic properties as rapamycin including inhibition of TOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 200, illustrated in FIG. 2, where the stent 200 makes contact with the lumen wall.

Rapamycin may be incorporated onto or affixed to the stent in a number of ways. In the exemplary embodiment, the rapamycin is directly incorporated into the polymeric matrix and the stent 200 is dip coated using the process described above. The rapamycin elutes from the polymeric matrix over time and enters the surrounding tissue. The rapamycin preferably remains on the stent for at least three days up to approximately six months, and more preferably between seven and thirty days.

As stated above, film forming or bridging across the open space between structural members of the medical device is of particular concern in dip coating processes. Complex shapes or geometries tend to facilitate bridging. For example, curvature in stent design tends to promote the formation of films. Film forming in the open spaces in stents may cause potential problems, including the prevention of tissue in-growth and the release of embolic causing material during stent expansion. Water has a high surface tension and does not readily form bridging films. Accordingly, the aqueous latex polymeric emulsion of the present invention is significantly less likely to form bridging film in a dip coating process.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for coating medical devices comprising the steps of:
   (a) preparing an aqueous latex polymeric emulsion of vinylidenefluoride and hexafluoropropolyene;
   (b) dipping a medical device in the aqueous latex polymeric emulsion;
   (c) drying the aqueous latex polymeric emulsion on the medical device to form a coating thereon; and
   (d) repeating steps (b) and (c ), at least once, until the aqueous latex polymeric emulsion coating reaches a predetermined thickness.

2. The method for coating medical devices according to claim 1, wherein the step of mixing vinylidenefluoride and hexafluoropropylene in water comprises adding vinylidenefluoride and hexafluoropropylene to the water in an approximately twenty-five to seventy-five ratio by weight.

3. The method for coating medical devices according to claim 1, wherein the step of drying the aqueous latex polymeric emulsion on the medical device to form a coating thereon comprises allowing the water to evaporate from the aqueous latex polymeric emulsion thereby depositing a film on the surface of the medical devices.

4. The method for coating medical devices according to claim 1, wherein the step of repeating steps (b) and (c) until the aqueous latex polymeric emulsion coating reaches a predetermined thickness comprises creating a coating in the range from about four to about fifteen microns.

5. A method for coating medical devices comprising the steps of:
   (a) preparing an aqueous latex polymeric emulsion of vinylidenefluoride and hexafluoropropylene;
   (b) adding at least one drug, agent and/or compound, in therapeutic dosages, to the aqueous latex polymeric emulsion for the treatment of a predetermined condition;
   (c) dipping the medical device in the aqueous latex polymeric emulsion, including the at least one drug, agent and/or compound;
   (d) drying the aqueous latex polymeric emulsion, including the at least one drug, agent and/or compound, on the medical device to form a coating thereon; and
   (e) repeating steps (c) and (d), at least once, until the aqueous latex polymeric emulsion, including the at least one drug, agent and/or compound coating reaches a predetermined thickness.

6. The method for coating medical devices according to claim 5, wherein the step of mixing vinylidenefluoride and hexafluoropropylene in water comprises adding vinylidenefluoride and hexafluoropropylene to the water in an approximately twenty-five to seventy-five ratio by weight.

7. The method for coating medical devices according to claim 5, wherein the step of adding at least one drug, agent and/or compound comprises adding an anti-proliferative.

8. The method for coating medical devices according to claim 7, wherein the step of adding at least one drug, agent and/or compound comprises adding rapamycin.

9. The method for coating medical devices according to claim 5, wherein the step of drying the aqueous latex polymeric emulsion, including the at least one drug, agent and/or compound, on the medical device to form a coating thereon comprises allowing the water to evaporate from the aqueous latex polymeric emulsion thereby depositing a film on the surface of the medical devices.

10. The method for coating medical devices according to claim 5, wherein the step of repeating steps (c) and (d) until the aqueous latex polymeric emulsion, including the at least one drug, agent and/or compound, coating reaches a predetermined thickness comprises creating a coating in the range from about four to about fifteen microns.

* * * * *